(12) United States Patent
Dennison

(10) Patent No.: US 7,754,256 B2
(45) Date of Patent: Jul. 13, 2010

(54) NUTRITIONAL COMPOSITION

(76) Inventor: Stan Dennison, 1222 8$^{th}$ St., Woodward, OK (US) 73801

( * ) Notice: Subject to any disclaimer, the term of this patent is extended or adjusted under 35 U.S.C. 154(b) by 6 days.

(21) Appl. No.: 12/074,863

(22) Filed: Mar. 6, 2008

(65) Prior Publication Data
US 2008/0220099 A1 Sep. 11, 2008

Related U.S. Application Data

(60) Provisional application No. 60/905,473, filed on Mar. 7, 2007.

(51) Int. Cl.
| A23G 1/00 | (2006.01) |
| A23L 1/31 | (2006.01) |
| A23L 1/315 | (2006.01) |
| B65D 81/34 | (2006.01) |
| A61K 36/00 | (2006.01) |
| A61K 36/899 | (2006.01) |
| A21D 13/00 | (2006.01) |
| A01N 43/04 | (2006.01) |
| A61K 31/70 | (2006.01) |
| A01N 43/08 | (2006.01) |
| A61K 31/34 | (2006.01) |

(52) U.S. Cl. ........................ 426/105; 426/138; 424/725; 424/750; 514/62; 514/474; 514/1

(58) Field of Classification Search ....................... None
See application file for complete search history.

(56) References Cited

U.S. PATENT DOCUMENTS

| 4,514,421 | A | * | 4/1985 | Herschler | ................... 514/711 |
| 5,045,339 | A | * | 9/1991 | Ducharme | ................... 426/641 |
| 6,156,335 | A | * | 12/2000 | Rovati et al. | ................. 424/448 |
| 6,716,458 | B1 | * | 4/2004 | Tarbet | ........................ 424/639 |
| 6,902,739 | B2 | * | 6/2005 | McPeak et al. | ............. 424/442 |
| 2002/0068718 | A1 | * | 6/2002 | Pierce | ........................... 514/54 |
| 2005/0013899 | A1 | * | 1/2005 | Kostlan et al. | ................. 426/2 |

FOREIGN PATENT DOCUMENTS

JP 2002095439 A * 4/2002

* cited by examiner

*Primary Examiner*—Amy L Clark
(74) *Attorney, Agent, or Firm*—Thomas A. O'Rourke; Booner & O'Rourke, LLP

(57) ABSTRACT

A dietary supplement for dogs is disclosed. The composition is a blend of methyl sulfonyl methane, glucosamine sulfate, chondroitin sulfate, ascorbic acid, phylloquinone, yucca powder and stabilized rice bran. The composition may be added to a variety of meat products for dogs, preferably beef and/or beef by-products.

13 Claims, No Drawings

NUTRITIONAL COMPOSITION

This application claims priority on U.S. Provisional Application Ser. No. 60/905,473 filed Mar. 7, 2007, the disclosures of which are incorporated herein by reference.

FIELD OF THE INVENTION

The present invention relates to improved dietary supplements for animals, particularly dogs. The dietary supplements of the present invention have particular applicability for relieving joint inflammation and joint pain in dogs.

BACKGROUND OF THE INVENTION

Many dogs have problems with their joints. These problems can include basic pains and inflammation. The joint problems can also include more serious issues including arthritis and rheumatism.

There are several factors that can cause joint pain. An injury is one of the more common causes of joint pain. Other causes can include poor nutrition, old age, lack of exercise, obesity and genetics. Some of the signs of joint pain in your dog can include unusual or awkward movements, stiffness, whimpering when sitting or standing, irritability. Other indicators are any swelling or thickening of the joints or an unwillingness to be stroked or petted, favoring a limb, inability to rise and a reluctance to jump or climb stairs. Any one or more of these conditions can indicate joint problems or perhaps a more serious health condition.

Conventional treatment of joint problems in dogs can include changing the dogs diet, incorporating regular exercise and taking anti-inflammatory drugs to ease swelling and pain. Anti-inflammatory drugs can have side effects that make many pet owners reluctant to use them. These side effects can include liver and kidney problems, vomiting, ulcers and excessive irritation. Because of these side effects, many dog owners are looking for alternative treatment for joint problems without the potential adverse reactions of the anti-inflammatory drugs.

SUMMARY OF THE INVENTION

The present invention is directed to improve joint functions for dogs. The present invention also has applicability in connection with reducing joint inflammation and joint pain in dogs. These compositions of the present invention are intended to supplement the dogs regular diet and provide the dog with more joint function. The composition of the present invention includes the following composition:

Methyl Sulfonyl Methane
Glucosamine Sulfate
Chondroitin Sulfate
Vitamin C (ascorbic acid)
Vitamin K (phylliquinone)
Yucca powder
Stabilized rice bran The foregoing composition may be used as an additive in a dog's food or can be further mixed with beef and beef by products such as the heart and/or the liver. Other materials can be added to the composition if desired. These include:

Carrots
Soy Sauce (Water, Salt, Hydrolyzed Soy Protein, Corn Syrup, Caramel Color)
Brown Sugar
Worcestershire Sauce (Distilled Vinegar, Molasses, Corn Syrup, Water, Salt, Caramel Color, Garlic Powder, Sugar, Spices, Anchovies, Tamarind, Natural Flavor), Liquid Smoke (Water, Natural Hickory Smoke Flavor)
Salt
Nonfat Milk
Garlic Powder
Onion Powder
Cayenne Pepper
Ginger The supplement of the present invention can be provided to the dog in a variety of forms. It is preferred, however, that the composition be made in accordance with the following steps:

Initially, the ingredients are combined preferably in a blender or similar device. Once the ingredients have been suitably blended, the composition may be stuffed into casings. The casings may be natural cellulosic based or other types of casings. The filled casings are frozen. Usually the casings are placed on racks where they are frozen. Once the filled casings are frozen, the casings are removed from the freezer where they are then sliced into thin disks or wafers called rounds. The rounds are placed on a rack where they are then cooked with heat under low humidity(dehydrator). The rounds may be cooked in the presence of a dehumidifier to provide the necessary drying. In a preferred embodiment, the rounds are preferably cooked in a smoker. When the cooking is completed, the rounds are removed from the oven. A sorbate mix with water is lightly misted onto the rounds. The sorbate mix can include a salt of a sorbic acid such as potassium sorbate or a calcium sorbate. The product is then allowed to cool and removed from the racks. The product is then packaged in any suitable container or packaging.

OBJECTS OF THE INVENTION

It is an object of the invention to provide an improved joint supplement for animals.

It is also an object of the invention to provide an improved joint supplement for canines such as dogs and the like.

It is an object of the invention to provide a joint supplement that has a taste that the recipients will enjoy.

It is an object of the invention to provide a dietary supplement that complements a dog's natural diet.

It is another object of the invention to provide a joint supplement that includes primarily natural ingredients.

It is a still further object of the invention to provide a dietary supplement that provides beneficial results to a recipient.

DETAILED DESCRIPTION OF THE INVENTION

The present invention is directed to improve joint function for dogs and other canines. This dietary supplement is intended to supplement the dogs regular diet. The composition of the present invention includes the following composition:

Methyl Sulfonyl Methane (an organosulfur compound with the formula $(CH_3)_2 SO_2$)—MSM is a nutriceutical that has been used for the skin and for pain relief. Methyl Sulfonyl Methane is a metabolite of DMSO (dimethyl sulfoxide). MSM is also known as dimethylsulfone ($DMSO_2$).

MSM is used to speed the recovery from exhaustion and over-training, and facilitates the repair of protein tissue through its bioavailable sulfur. MSM keeps cells from becoming rigid. MSM softens tissue, and is believed to relieve stress, asthma, arthritis, inflammation, constipation, candida, detoxify the body and increase blood circulation, reduce muscle cramps, and back pain, help muscles to heal, increases energy, alertness, mental calmness, and the ability to concentrate. MSM scavenges free radicals, relieves allergies to food and pollens, helps the liver produce choline, controls acidity in stomach and ulcers, coats intestinal tract so parasites lose ability to hang on, helps with hypersensitivity to drugs, increases body's ability to produce insulin, is important for carbohydrate metabolism, and speeds wound healing. The composition of the present invention has at least 0.001% by weight of Methyl Sulfonyl Methane. In a preferred composition, the amount of MSM is no more than about 1% of the composition by weight.

Glucosamine Sulfate (also known as glucosamine)sulphate—Glucosamine $C_6H_{13}NO_5$ is an amino sugar and is a major component of exoskeletons of crustaceans and arthropods. It is also found in fungi. Glucosamine salts have been studied extensively for treating osteoarthritis, a condition that generally results from wear-and-tear on joints. In osteoarthritis, deterioration of the cartilage, which cushions the joints, leads to pain, swelling, and loss of movement. Since glucosamine provides a major component of cartilage, it is believed that supplemental glucosamine may delay further degeneration. It may also actually help to repair deteriorating cartilage. The composition of the present invention has at least 0.001% by weight of a glucosamine salt preferably Glucosamine Sulfate. The composition preferably has no more than about 1% by weight of the Glucosamine Sulfate.

Chondroitin Sulfate—Chondroitin sulfate belongs to a family of heteropolysaccharides called glycosaminoglycans or GAGs. Glycosaminoglycans were formerly known as mucopolysaccharides. GAGs in the form of proteoglycans comprise the ground substance in the extracellular matrix of connective tissue. Chondroitin sulfate is made up of linear repeating units containing D-galactosamine and D-glucuronic acid. Chondroitin sulfate is found in cartilage, bone, cornea, skin and the arterial wall. Chondroitin Sulfate is preferably present in the composition of the present invention in an amount of at least 0.001% by weight. The composition preferably has no more than about 1% by weight Chondroitin Sulfate Vitamin C, ascorbic acid, is present in the composition of the present invention in amount of at least 0.001% by weight of the overall composition. The composition preferably has no more than about 1% by weight ascorbic acid.

Beef is present in the composition in the amount of at least 0.001% by weight of the overall composition.

Beef Heart is present in the composition of the present invention in amount of at least 0.001% by weight of the overall composition.

Beef Liver is present in the composition of the present invention in amount of at least 0.001% by weight of the overall composition.

Vitamin K, phylliquinone, is present in the composition of the present invention in an amount of at least 0.001% by weight of the overall composition. The vitamin K may be present as either the phylloquinone or menaquinone. The vitamin K based compounds typically have a methylate napthoquinone ring structure and vary in the aliphatic side chain attached at the three position. The composition preferably has no more than about 1% by weight vitamin K.

In addition to the foregoing, the composition may include one or more of the following materials:

Carrots may be present in the composition of the present invention in amount of at least 0.001% by weight of the overall composition.

Soy Sauce (Water, Salt, Hydrolyzed Soy Protein, Corn Syrup, Caramel Color) may be present in the composition of the present invention in amount of at least 0.001% by weight of the overall composition.

Brown Sugar may be present in the composition of the present invention in amount of at least 0.001% by weight of the overall composition.

Worcestershire Sauce (Distilled Vinegar, Molasses, Corn Syrup, Water, Salt, Caramel Color, Garlic Powder, Sugar, Spices, Anchovies, Tamarind, Natural Flavor) may be present in the composition of the present invention in amount of at least 0.001% by weight of the overall composition.

Liquid Smoke (Water, Natural Hickory Smoke Flavor) may be present in the composition of the present invention in amount of at least 0.001% by weight of the overall composition.

Salt may be present in the composition of the present invention in amount of at least 0.001% by weight of the overall composition.

Nonfat Milk may be present in the composition of the present invention in amount of at least 0.001% by weight of the overall composition.

Garlic Powder may be present in the composition of the present invention in amount of at least 0.001% by weight of the overall composition.

Onion Powder may be present in the composition of the present invention in amount of at least 0.001% by weight of the overall composition.

Yucca Powder may be present in the composition of the present invention in amount of at least 0.001% by weight of the overall composition. The yucca powder is an extract of Yucca Schidigera.

Cayenne Pepper may be present in the composition of the present invention in amount of at least 0.001% by weight of the overall composition.

Ginger may be present in the composition of the present invention in amount of at least 0.001% by weight of the overall composition.

Stabilized Rice Bran may be present in the composition of the present invention in amount of at least 0.001% by weight of the overall composition.

In addition, there may be other materials added to the composition if desired.

Formation of the Dietary Supplement Composition

The supplement of the present invention can be provided to the dog in a variety of forms. It is preferred, however, that the composition be made in accordance with the following steps:

Initially, the ingredients are combined preferably in a blender or similar device. Once the ingredients have been suitably blended, the composition may be stuffed into casings. The casings may be natural cellulosic based or other types of casings. The filled casings are frozen. Usually the casings are placed on racks where they are frozen. Once the filled casings are frozen, the casings are removed from the freezer where they are then sliced into thin disks or wafers called rounds. The rounds are placed on a rack where they are then cooked with heat under low humidity (dehydrator). The rounds may be cooked in the presence of a dehumidifier to provide the necessary drying. In a preferred embodiment, the rounds are preferably cooked in a smoker. When the cooking is completed, the rounds are removed from the oven. A sorbate mix with water is lightly misted onto the rounds. The product is then allowed to cool and removed from the racks. The product is then packaged in any suitable container or packaging.

A preferred composition for the present invention is as follows:

methyl sulfonyl methane 0.001% by weight to about 50% by weight glucosamine sulfate 0.001% by weight to about 50% by weight chondroitin sulfate 0.001% by weight to about 50% by weight ascorbic acid 0.001% by weight to about 50% by weight
phylloquinone 0.001% by weight to about 50% by weight
yucca powder 0.001% by weight to about 50% by weight
stabilized rice bran 0.001% by weight to about 50% by weight The balance may be a meat such as beef and beef by products
More preferably, the composition may be as follows:
methyl sulfonyl methane 0.1% by weight to about 25% by weight
glucosamine sulfate 0.1% by weight to about 25% by weight
chondroitin sulfate 0.1% by weight to about 25% by weight
ascorbic acid 0.1% by weight to about 25% by weight
phylloquinone 0.1% by weight to about 25% by weight
yucca powder 0.1% by weight to about 25% by weight
stabilized rice bran 0.1% by weight to about 25% by weight The balance may be a meat such as beef and beef by products In another preferred embodiment the composition may be as follows:

Another preferred composition for the present invention is as follows:
methyl sulfonyl methane 0.1% by weight to about 5% by weight
glucosamine sulfate 0.1% by weight to about 5% by weight
chondroitin sulfate 0.1% by weight to about 5% by weight
ascorbic acid 0.1% by weight to about 5% by weight
phylloquinone 0.1% by weight to about 5% by weight
yucca powder 0.1% by weight to about 5% by weight
stabilized rice bran 0.1% by weight to about 5% by weight The balance of the composition is beef and beef by-products. The beef by-products are preferably the heart and the liver. Other ingredients can be added to the composition of the present invention.

I claim:

1. A method of forming a dietary supplement for dogs, for use in the treatment of joint inflammation and joint pain, said dietary supplement comprising:

forming a blend consisting essentially of methyl sulfonyl methane, glucosamine sulfate, chondroitin sulfate, ascorbic acid, phylloquinone, yucca powder and stabilized rice bran;
adding said blend to beef and beef by-products;
mixing said blend, beef, and beef by-products;
stuffing said beef, and beef by-products into a casing;
freezing said filled casings;
slicing said filled casings into disks; and
cooking said disks with heat under low humidity.

2. The method according to claim 1 wherein said disks are sliced very thin to form wafers, and wherein said wafers are cooked in a smoker.

3. The method according to claim 1 wherein said wafers are misted with a blend of water and a sorbate.

4. The method according to claim 3 wherein said beef by-products comprise one or more of beef heart and beef liver.

5. The method according to claim 4 wherein said blend further comprises carrots.

6. The method according to claim 5 wherein said blend further comprises soy sauce.

7. The method according to claim 6 wherein said blend further comprises brown sugar.

8. The method according to claim 7 wherein said blend further comprises Worcestershire Sauce.

9. The method according to claim 8 wherein said blend further comprises Liquid Smoke.

10. The method according to claim 9 wherein said blend further comprises salt.

11. The method according to claim 10 wherein said blend further comprises one or more of nonfat milk, garlic powder, onion powder, cayenne pepper, and ginger.

12. The method according to claim 11 wherein said casing comprises a natural cellulose casing.

13. The method according to claim 12 wherein said soy sauce comprises water, salt, hydrolyzed soy protein, corn syrup, and caramel color.

* * * * *